(12) United States Patent
Childers et al.

(10) Patent No.: US 7,275,534 B2
(45) Date of Patent: Oct. 2, 2007

(54) MEDICAMENT EJECTOR WITH EJECTION PORT SERVICING

(75) Inventors: Winthrop D Childers, San Diego, CA (US); David Tyvoll, La Jolla, CA (US); Steven W. Steinfield, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 991 days.

(21) Appl. No.: 10/356,077

(22) Filed: Jan. 31, 2003

(65) Prior Publication Data

US 2004/0150690 A1 Aug. 5, 2004

(51) Int. Cl.
- *A61M 11/00* (2006.01)
- *A61M 15/00* (2006.01)
- *A61M 16/00* (2006.01)
- *A62B 7/00* (2006.01)
- *A62B 9/00* (2006.01)
- *A62B 18/00* (2006.01)

(52) U.S. Cl. .......................... 128/200.14; 128/200.13; 128/200.23; 128/200.24

(58) Field of Classification Search ................ 128/200.12–200.14, 200.23, 203.12, 203.14, 128/203.15, 203.21, 203.27, 201.16, 200.24; 347/29, 33; 239/104, 106, 114, 123; 222/148, 222/149, 402.12; 345/440–440.2; 715/771
See application file for complete search history.

(56) References Cited

U.S. PATENT DOCUMENTS

| | | | |
|---|---|---|---|
| 2,434,875 A | 1/1948 | Hamilton et al. | |
| 3,484,023 A * | 12/1969 | Meshberg | 222/402.11 |
| 4,853,717 A | 8/1989 | Harmon et al. | |
| 5,103,244 A | 4/1992 | Gast et al. | |
| 5,115,250 A | 5/1992 | Harmon et al. | |
| 5,207,785 A * | 5/1993 | Knickerbocker | 222/148 |
| 5,240,502 A * | 8/1993 | Castaldo et al. | 118/302 |
| 5,331,953 A | 7/1994 | Andersson et al. | |
| 5,337,926 A * | 8/1994 | Drobish et al. | 222/309 |
| 5,500,660 A | 3/1996 | Childers et al. | |
| 5,563,638 A | 10/1996 | Osborne | |
| 5,621,441 A | 4/1997 | Waschhauser et al. | |
| 5,812,157 A | 9/1998 | Nguyen et al. | |
| 5,881,716 A | 3/1999 | Wirch et al. | |
| 5,894,841 A | 4/1999 | Voges | |
| 5,927,558 A * | 7/1999 | Bruce | 222/185.1 |
| 5,946,009 A * | 8/1999 | Youn | 347/32 |
| 6,325,475 B1 | 12/2001 | Hayes et al. | |
| 6,390,453 B1 | 5/2002 | Frederickson et al. | |
| 6,460,537 B1 | 10/2002 | Bryant et al. | |
| 2002/0109744 A1 | 8/2002 | Shindo | |
| 2004/0107961 A1* | 6/2004 | Trueba | 128/200.16 |
| 2004/0135842 A1* | 7/2004 | Saksa | 347/33 |

* cited by examiner

*Primary Examiner*—Justine R. Yu
*Assistant Examiner*—Kristen Matter

(57) ABSTRACT

A medicament ejector is provided which includes an ejection mechanism and a service mechanism. The ejection mechanism includes at least one ejection port configured to eject a medicament-containing fluid. The service mechanism is selectively deployable to service the at least one ejection port.

6 Claims, 4 Drawing Sheets

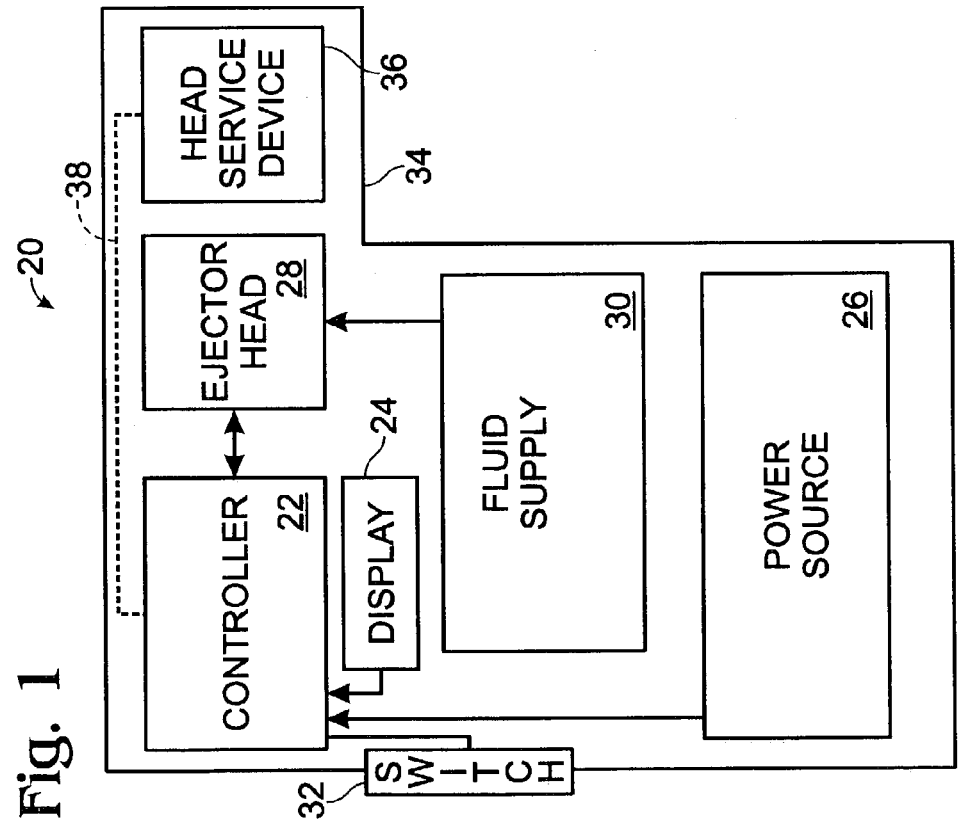

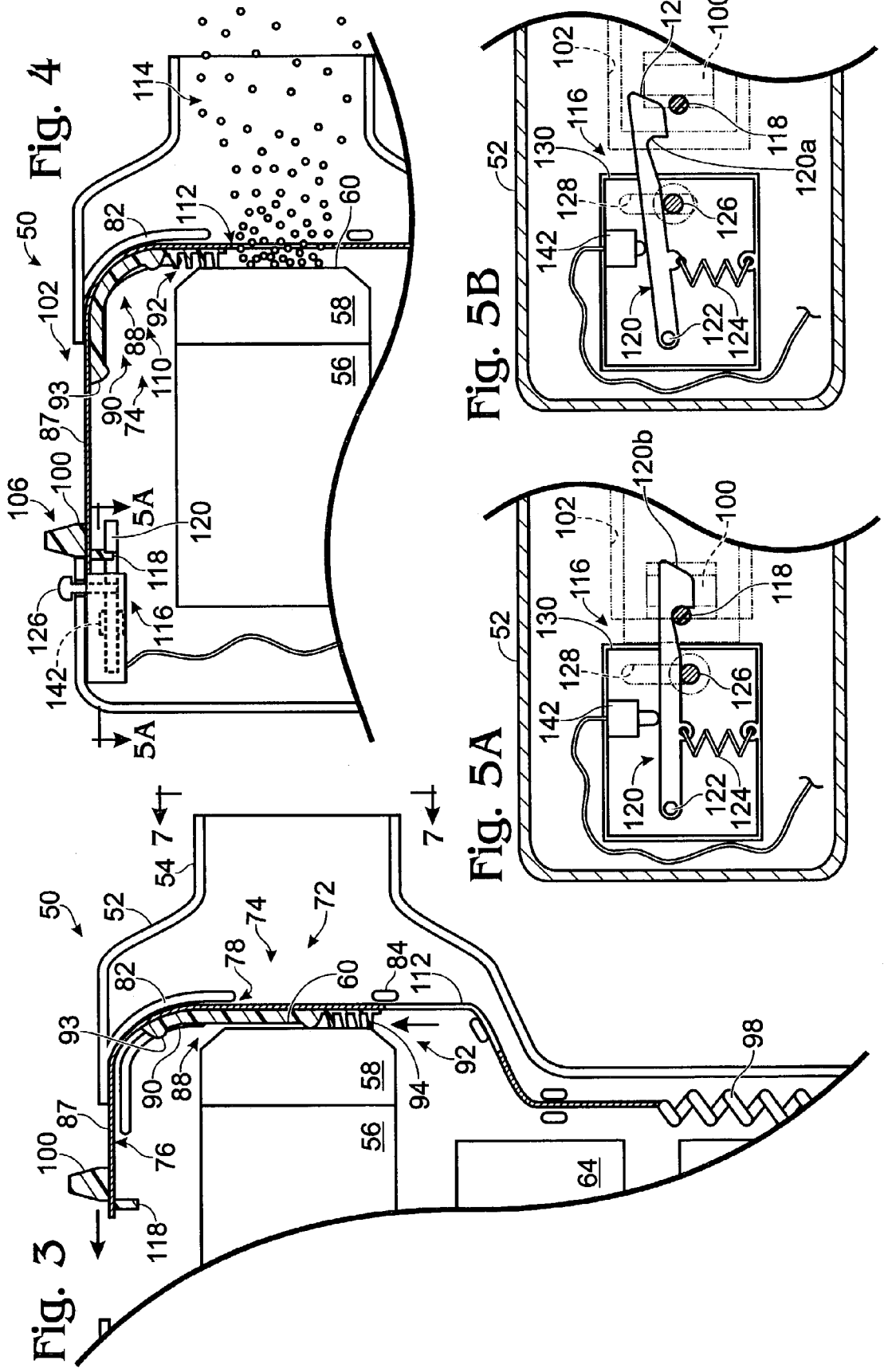

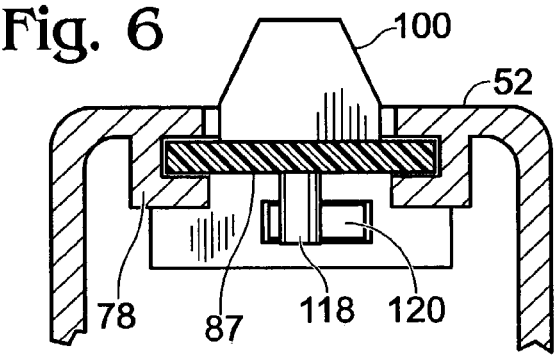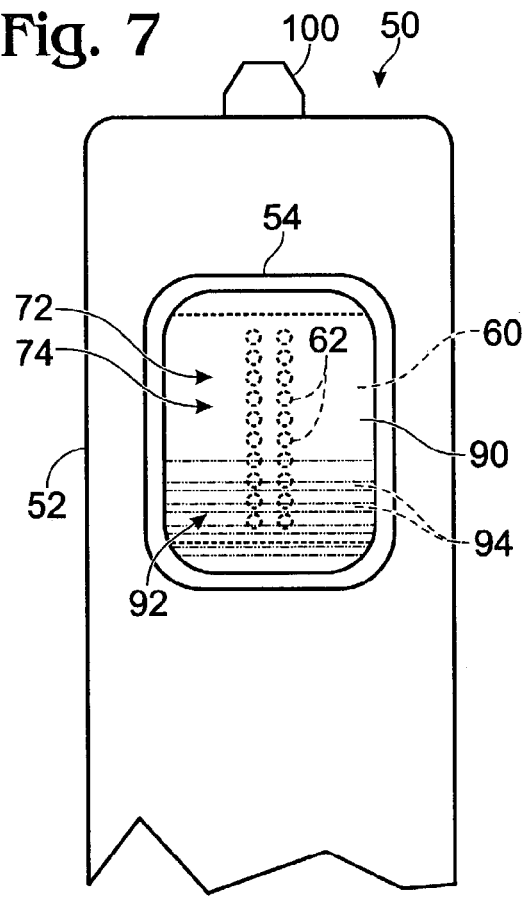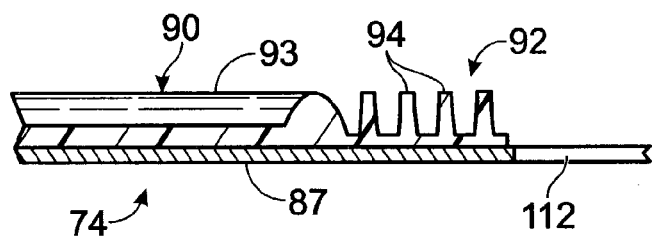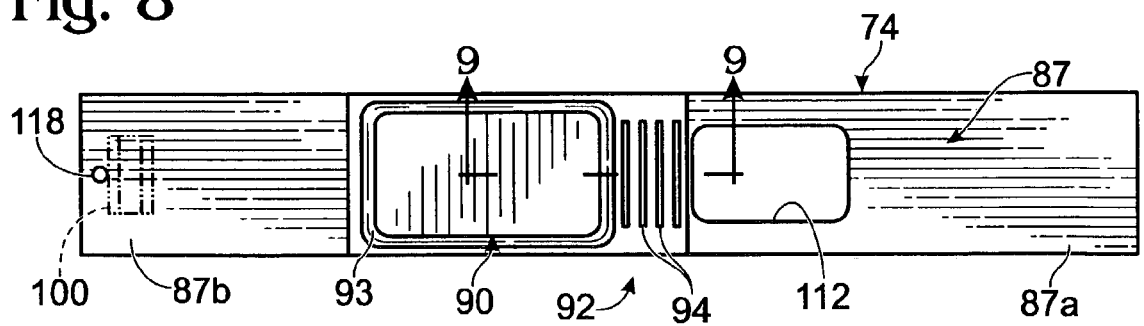

US 7,275,534 B2

MEDICAMENT EJECTOR WITH EJECTION PORT SERVICING

BACKGROUND

There are various techniques used to dispense medicament as an aerosol. These techniques provide much-needed drug-delivery methods that allow patients to aspirate medication rather than swallow a pill, or drink or inject medication. In some cases, as with medications that directly target the patient's lungs, aspiration enables the medicine to reach the target area more quickly. In addition, aspiration is typically considered to be less painful than other drug-delivery methods.

Examples of aerosol dispensers include metered dose inhalers, dry powder inhalers, and nebulizers. Each of these typically has at least a single nozzle, if not multiple nozzles from which the aerosol medicament may be ejected. With any of these devices, effective and consistent ejection of controlled doses of medicament may be achieved where the one or more nozzles are free of debris and medicament build-up. When any form of blockage of a nozzle occurs, inconsistent and incomplete doses may be dispensed. Further, blockages can transform the character of the ejected aerosol, such as altering the size and quantity of drops ejected. Accordingly, it is desirable to use medicament ejectors that have clean nozzles to assure that desired doses are dispensed.

SUMMARY

A medicament ejector is provided which includes an ejection mechanism and a service mechanism. The ejection mechanism includes at least one ejection port configured to eject a medicament-containing fluid. The service mechanism is selectively deployable to service the at least one ejection port.

BRIEF DESCRIPTION OF THE DRAWINGS

FIG. 1 is a side view in block diagram form of a medicament ejector according to an embodiment of the present invention.

FIG. 2 is a side view in partial block diagram form of a medicament ejector in a first operating state according to another embodiment of the present invention.

FIG. 3 is a partial side view of a portion of an ejector similar to the ejector of FIG. 2 showing a second operating state.

FIG. 4 is a view similar to FIG. 3 showing a third operating state.

FIG. 5A is an enlarged top view of a portion of the ejector of FIG. 4 taken along line 5-5 of FIG. 4.

FIG. 5B is a view similar to FIG. 5A, but showing a different operating position.

FIG. 6 is a cross section taken along line 6-6 of FIG. 2.

FIG. 7 is an end view taken along line 7-7 of FIG. 3.

FIG. 8 is a plan view of a service assembly of the ejector of FIG. 3.

FIG. 9 is a cross section taken along line 9-9 of FIG. 8.

DETAILED DESCRIPTION

Figure 10:
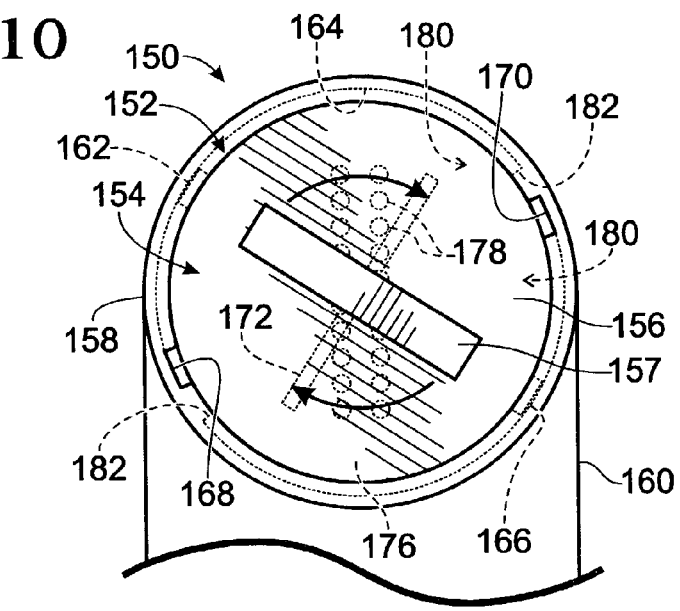
FIG. 10 is an end view illustrating operation of a portion of a medicament ejector made according to another embodiment of the present invention.

Referring initially to FIG. 1, a medicament ejector made according to an embodiment of the present invention is shown generally at 20. Ejector 20 may eject a medicament as an aerosol, such as is provided by a metered dose inhaler, a dry powder inhaler, or a nebulizer. As a metered dose inhaler, it may be a bubble-jet, piezoelectric or vibrating-membrane type. The medicament may be entrained or otherwise mixed, such as in solution in a gas or liquid fluid. Accordingly, such a medicament may also be referred to as a fluid-based solute medicament.

As shown, ejector 20 may include a controller 22 adapted to control ejector 20 electronically, mechanically, or both. Controller 22 thus may include a processor and memory configured to store preprogrammed operating parameters. The memory may include volatile memory, nonvolatile memory, or both. It is to be appreciated that such operating parameters may be provided via direct user input, may occur via a personal computer or other device, or may be in the form of firmware. The controller may provide a prescribed dosage or nominal dosage, and/or may be provided with dosage parameters such as a loading dosage and/or a dosing regimen set by a physician, pharmacist, or manufacturer of the prescribed medicament.

Dosage information as well as audible or visible alarm conditions, and other desired information may be communicated to a display 24 for communication with a user. Controller 22, which may also be referred to as structure for controlling operation, typically receives power from a power source 26. The power source may be a battery, external power source, or other suitable power supply, whether disposable, rechargeable or permanent.

As indicated, controller 22 also may be in electronic communication with an ejector head 28, also referred to as an ejection mechanism, so as to provide controlling direction to one or more ejection elements to effect controlled ejection of droplets of medicament as an aerosol. Head 28 may also be referred to as structure for ejecting medicament. The ejection elements receive fluid-based medicament from a fluid supply 30, also referred to as structure for storing medicament.

Operation of the ejector may be initiated by an activation switch 32 controlled by the user, or the ejector may instead detect the presence of the user, such as through inhalation through a mouthpiece 34, and activate the inhaler automatically.

Ejector 20 also may include a head service device, or service mechanism 36, which provides structure for servicing the ejector head. The servicing may be virtually any function that maintains, repairs or otherwise adjusts an aspect of the ejector head to promote extended operation as designed. The head service device may provide a signal to controller 22 on a line 38 indicative of some aspect of the servicing function. The controller may then control operation of the ejector head based on the information contained in the signal. For instance, operation of the ejector head may be blocked if the service function has not been performed since the last operation of the ejector head, or if the service device is in a position that may interfere with operation of the ejector head.

Referring now to FIGS. 2-9, another embodiment of a medicament ejector is shown generally at 50. Ejector 50 includes a housing 52 having a mouthpiece 54 that provides an exit passage for the ejected inhalant. A fluid supply 56 typically stores medicament and provides it to ejection chambers in ejector head 58. Ejector head 58 may have an ejection face 60 with one or more ejection ports 62, shown in FIG. 7. The ejection face and ports may be formed as part of a rigid plastic or metal base, by a porous membrane supported over one or more ejection chambers from which medicament is ejected, or by other suitable structure. The ejection face may be a continuous smooth surface in which the ports are located, which surface may be planar, curved, or have another shape. Ports 62 may also be referred to as apertures, orifices, openings, or structure for allowing the passage of medicament. The ports may allow medicament ejected from the ejection head to pass out of ejector head 58 and into mouthpiece 54 for inhalation by a user, and may also have any suitable shape and arrangement.

A controller 64, that may receive power from a battery pack 66, may control operation of the ejector head. An activation switch 68 controlled by the user may be used to initiate operation of the ejector. An alarm 70 may be used to notify the user of the operating condition of the ejector, such as when medicament supplies are getting low or when functioning of the ejector is interrupted.

The ejector also may include a head service device 72 designed to service ejector head 58. Service device 72 may include a service assembly 74 that may be formed as an integral continuous ribbon, as shown in FIG. 2. This ribbon may be flexible, or have articulating elements, to allow movement along a non-rectilinear path 76, such as is defined by a track 78 that may be formed in or supported on housing 52. Track 78 may be formed by guides, such as guides 80, 82, 84 and 86. Alternatively, and optionally, if the movement does not require flexing, assembly 74 may be rigid.

Service assembly 74 may include a carrier 87 and service mechanism shown generally at 88 that may include a capper 90 and a wiper 92. Capper 90, also referred to as structure for capping, may include a ridge 93 that extends around the perimeter of the ejection ports. Ridge 93 may sealingly and selectively engage ejection face 60 in order to environmentally isolate the ports from ambient conditions when the ejector is not in use. This may maintain the humidity around the ports, preventing drying of any residual medicament. Other benefits of the capper may include preventing depriming of any ejection chambers if the ejector is dropped, and preventing environmental debris from covering the ejection face. Wiper 92 may be formed of a plurality of ridges or blades, such as blade 94, extending laterally across the width of the ejection face. Wiper 92, also referred to as structure for cleaning or wiping, may wipe the ejection ports 62, as shown in FIGS. 3 and 7, and may remove residual medicament or other debris resident around the ejection ports or on the ejection face. This may keep the ports clear so that ejection of medicament during operation of the ejector head is unimpeded.

Service mechanism 88 may be made of an elastomeric or resilient material, such as an EPDM rubber, or other material capable of performing the associated service function or functions, such as capping and wiping. As shown in FIG. 3, the service mechanism may be mounted or supported on carrier 87 that may be made of the same material as the service mechanism. In this case, the carrier may be made integrally with the service mechanism as shown in FIG. 2. Alternatively, the carrier may be made of a durable, flexible and non-stretchable material, such as a sheet metal, plastic or a fabric that is different than the material from which the service mechanism is made. This embodiment is shown in FIGS. 3, 4, 8 and 9. For example, the carrier could be made of a thin layer of a metal such as spring steel, plastic or fabric.

Carrier 87 may have an anchor end 87a that may be supported relative to the housing by the parallel connection of a dashpot 96 and a tension spring 98, as shown. The opposite or free end 87b of the carrier may be attached to a handle 100 that extends outwardly from housing 52 through a slot 102. Handle 100 may be engaged by a user and shifted between a first position 104, shown in FIG. 2, in which capper 90 is in a stored position covering ejection face 60, and a second position 106, shown in FIG. 4. When the handle is in the second position, the capper and wiper may be removed from a stored position 108 (FIG. 2) adjacent to the ejector face to a retracted position 110 (FIG. 4) spaced from the ejector face. The handle may thus function as structure for moving or deploying the service mechanism.

During movement of the service mechanism between the stored position and the retracted position, an action that also may be referred to as deploying the service mechanism, wiper 92 may move across ejection face 60, wiping the ejection ports in the face, as is illustrated in FIGS. 3 and 7. Carrier 87 may define an enlarged opening 112 that may be aligned with the ejection face when the service mechanism is in the retracted position. Opening 112 thus may allow medicament ejected from ejector head 58, as represented by ejection stream 114 in FIG. 4, to be ejected from the ejector.

A latch 116 may secure the service mechanism in the retracted position. A top view of latch 116, also referred to as structure for maintaining the service mechanism in a retracted position, is shown in FIGS. 5A and 5B. The distal or free end 87b of carrier 87 may have a pin 118 that may be secured by a notch or detent 120a in a lever arm 120. One end of the lever arm may pivot about pivot 122. Arm 120 may be biased toward a locking position, shown in FIG. 5A, by a biasing element, such as a spring 124. A tapered leading edge 120b of the lever arm may be initially contacted by pin 118 as carrier 87 is moved toward the retracted position. This may move the lever arm into a release position, shown in FIG. 5B, that allows movement of pin 118 along the side of the arm. When the pin reaches the detent in the lever arm, spring 124 may bias the arm into the locking position in which the pin and carrier may be prevented from moving toward the store position.

A release arm 126, may have a top end exposed for manipulation by a user. Arm 126 travels in a groove 128 in a frame 130 that is transverse to lever arm 120. After operation of the ejector, a user may release pin 118 by moving the release arm against the lever arm to a position such as that shown in FIG. 5B. When the pin is released, the carrier is free to move in track 78. Return spring 98, attached to the carrier end 87a, may bias the carrier, and thereby the service mechanism, toward the stored position, shown in FIG. 2. Optional dashpot 96 may be used to control the speed of movement of the wiper as it wipes across ejection face 60. For a relatively constant force, the dashpot may cause the wiper to move at a relatively constant speed during the wiping process. This may provide an improved wiping action that more effectively cleans the ejection ports than does a faster or variable speed wiping action.

Alternatively, release arm 126 may be automatically moved to release the lever arm by a powered mechanism controlled by controller 64, such as a solenoid, not shown. This automatic release may be effected after the ejector head has ejected a dose of medicament. When released, service mechanism 88 may be returned to the stored position, wiping the ejector face in the process. In this way, the wiping and capping functions may occur substantially immediately after the medicament ejection, and cleaning and sealing may be provided before any residual medicament has had an opportunity to dry or cake around the ejection ports.

It will also be appreciated that even without latch 116, service mechanism 88 may be moved or deployed between the stored and retracted positions by manipulation of handle 100 by a user. Alternatively, the service assembly may be moved along track 78 by operation of a gear, cogwheel or pinion 132 acting on teeth, such as tooth 134, formed in or attached to the backside of carrier 87, as shown. Pinion 132 may be rotated manually, such as by a handle 136 or an exposed rotating thumb wheel, not shown. The pinion may also be driven by a motor 138, such as a stepper motor. This drive assembly may also be referred to as structure for mechanically driving or deploying the service mechanism along the ejection face. When a motor is used, the position of the service mechanism may be determined from the operation of the motor, so the latch, spring, dashpot, and sensors may be omitted.

A sensor 140 may detect when the service mechanism has serviced the ejection ports, or when the service mechanism is retracted from the ejection face to allow for ejection of medicament from the ejection head. Sensor 140 may include a detection mechanism, such as a switch 142 (FIGS. 5A and 5B) that may be actuated when lever arm 120 moves from the release position into the locking position, as occurs when pin 118 docks into detent 120a, as explained above. Alternatively, sensor 140 may be placed at other locations along path 76 to detect movement of service mechanism 88 relative to ejection face 60.

A user may activate control switch 68 to initiate operation of ejector 50, if automatic activation is not provided. Initially, controller 64 may determine, from sensor 140, whether the service mechanism is in the retracted position. The controller may prohibit operation of the ejector head during servicing, while the service mechanism is in the stored position, or during travel of the service mechanism between the stored and retracted positions. The controller may check the signal received from sensor 140 periodically. If handle 100 is used by the user to move the service mechanism to the retracted position, this movement may be detected by the operation of sensor switch 142, as discussed above. Alternatively, upon activation of control switch 68 by the user, a driver, such as motor 138, may move the service mechanism. During movement of the service mechanism 88 from the stored position to the retracted position, wiper 92 may wipe ejection face 60, cleaning debris from ejection ports 62.

On detection of the securing of pin 118 in detent 120a of the lever arm (e.g., via sensor 140), controller 64 may operate ejector head 58, causing medicament to be expelled from the ejector head and out of ports 62 for inhaling by the user. After completion of the medicament ejection, the user or an automatic device may disengage pin 118 by movement of release arm 126. Once released, the service mechanism may be returned to the stored position, and in doing so, may wipe the ports in ejection face 60 with wiper 92 and may cap the ejection face around the ejection ports with capper 90. The service mechanism may be returned to the stored position by manually moving handle 100 to the position shown in FIG. 2. Alternatively, spring 98 may draw the service mechanism back along track 78 to the stored position, or a motor 138 or manual device, such as handle 136 acting on pinion 132, may move the service mechanism.

An alternative embodiment of an ejector, shown generally at 150 in FIG. 10, includes a service device 152 including a service mechanism 154. Other features of the ejector may be similar to those described above for other embodiments. As shown, service mechanism 154 includes a cap 156, having a handle 157, that may be attached to a mouthpiece 158 of a housing 160 of ejector 150, such as by the capture of a knob 162 on the cap or mouthpiece that is captured in a circumferential groove 164 of the mouthpiece or cap, respectively. Service mechanism 154 may be held in place by knobs 162 and 166 extending from opposite sides of cap 156. Cap 156 is placed in an entry position by insertion of the cap in the mouthpiece, with knobs 162 and 166 aligned with openings 168 and 170 in the inside walls of the mouthpiece, as shown in the illustration.

When the cap is placed in the entry position with the knobs aligned with internal circumferential groove in the mouthpiece, a wiper or blade 172 contacts an ejection face 176 having ejection ports 178 on an ejector head 180. The cap is then rotated in place as represented by the arrows. The groove may have one or more stops 182 that limit the travel of the knobs. When the knobs reach the end of travel in the groove, the ports may have been wiped and the cap may be in a stored position with the ejection ports sealed.

The user may then reverse this process to use the ejector. During removal of the cap, the blade may again wipe the ports. It will be appreciated that other configurations of ejection ports, ejection face, wiper and cap structures may be used. For instance, the axis of rotation of the cap could be off center from a port or an array of ports, and the ports may be configured differently, such as in an arc, instead of a straight line. Also, sensors may be used to detect the presence and position of the cap or wiper.

Figure 11:
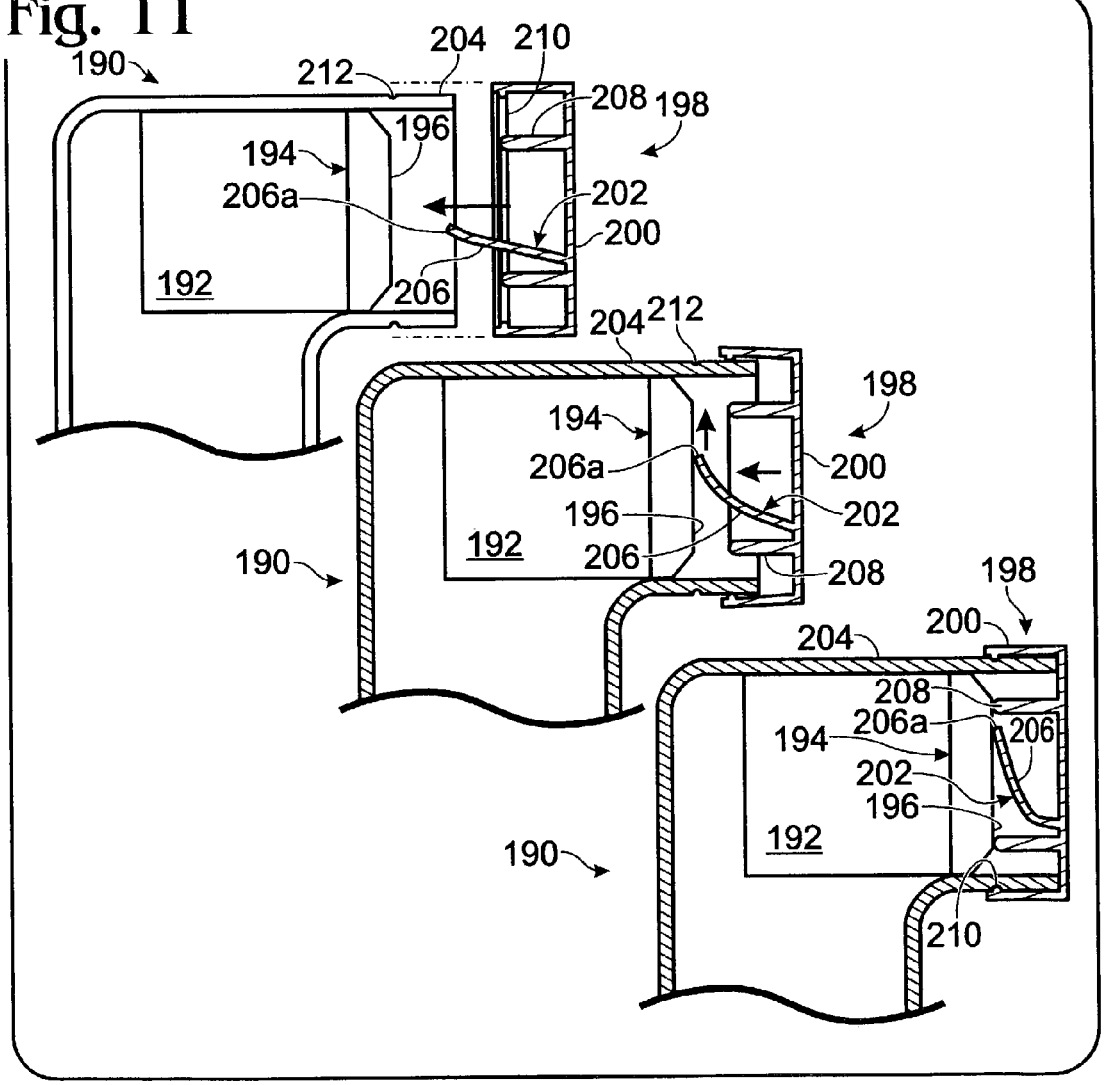
FIG. 11 is a series of side views illustrating operation of a portion of a medicament ejector made according to yet another embodiment of the present invention.

Another embodiment of an ejector is shown generally at 190 in FIG. 11. Ejector 190 may include a fluid supply 192 in fluid communication with an ejector head 194. Ejector head 194 may have an ejection face 196 through which may extend ejection ports similar to those described previously. Other ejector features also may be as described previously. A dual-purpose service mechanism 198, including a cap 200 and a wiper 202, is shown in different stages of positioning the cap on a mouthpiece 204 of the ejector.

Wiper 202, may include a blade 206 that may extend toward and contact the ejection face when the cap has been partially inserted, as shown in the middle illustration. Blade 206 may be formed of resilient material, and may be inclined or curved so that it may be oriented at an angle to the ejection face as it contacts the ejection face. As the cap is inserted onto or into the mouthpiece, a distal edge 206a of blade 206 may slide along the ejection face, cleaning away debris that exists on the ejection face or around the ejection port or ports. The cap and mouthpiece may thus be referred to as structure for deploying the service mechanism transverse to the ejection face. When the cap is placed on the mouthpiece to its furthest extent, a circumferential rim 208 of the cap, extending toward the ejection face, may contact the ejection face, surrounding and sealing the ejection ports. The cap may be held in place on the mouthpiece by a ridge 210 that snaps into a groove 212, as shown, or any other mechanism that secures the cap on the mouthpiece. Removal of the cap may reverse this process, with blade 206 wiping the ejection ports again.

As indicated by the embodiments disclosed, it will be appreciated that ejectors and associated service mechanisms may have varying forms and may perform varying functions. For instance, an active washing function may be provided, or a device may be provided that is inserted into or against the ejection ports to clean or seal them.

It is believed therefore that the disclosure set forth above encompasses multiple distinct embodiments. While each of these embodiments has been disclosed in specific form, the specific embodiments thereof as disclosed and illustrated herein are not to be considered in a limiting sense as numerous variations are possible. The subject matter of this disclosure thus includes all novel and non-obvious combinations and sub-combinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

What is claimed is:

1. An inhaler comprising:
   a supply of a fluid containing a medicament;
   an ejection mechanism including a face having a plurality of ejection ports, each port having an associated ejection chamber coupled to the fluid supply and configured to eject medicament-containing fluid;
   a wiper configured to travel along the face of the ejection mechanism; and
   a drive mechanism configured to move the wiper between a retracted position in which the plurality of ejection ports are exposed to allow the ejection mechanism to eject the medicament-containing fluid and a deployed position whereby the wiper wipes the face of the ejection mechanism along the ejection ports.

2. The inhaler of claim 1, wherein the drive mechanism includes a handle adapted to be manipulated to move the wiper between the retracted and deployed positions.

3. The inhaler of claim 1, further comprising a controller configured to control operation of the ejection mechanism, and wherein the drive mechanism includes a sensor configured to determine whether the wiper is in the retracted position, the controller being further configured to prohibit operation of the ejection mechanism unless the wiper is in the retracted position.

4. The inhaler of claim 1, further comprising a capper joined with the wiper, the drive mechanism being further configured to move the wiper through the deployed position to a store position, and wherein the wiper wipes the face of the ejection mechanism during movement between the retracted position and the store position, and the capper caps the plurality of ejection ports upon the wiper reaching the store position.

5. The medicament ejector of claim 1, wherein the drive mechanism is configured to deploy the wiper at a substantially constant speed.

6. The medicament ejector of claim 1, further comprising a controller configured to prohibit operation of the ejection mechanism while the wiper is deployed.

* * * * *